(12) United States Patent
Solomon

(10) Patent No.: US 10,688,301 B2
(45) Date of Patent: Jun. 23, 2020

(54) DEVICE AND METHODS FOR DELIVERY OF STIMULATION TO A BODY TISSUE

(71) Applicant: Sasi Solomon, Herzliya (IL)

(72) Inventor: Sasi Solomon, Herzliya (IL)

(73) Assignee: SYNAPSTIM LTD., Herzliya (IL)

( * ) Notice: Subject to any disclaimer, the term of this patent is extended or adjusted under 35 U.S.C. 154(b) by 424 days.

(21) Appl. No.: 15/328,276

(22) PCT Filed: Jul. 23, 2015

(86) PCT No.: PCT/IL2015/050763
§ 371 (c)(1),
(2) Date: Jan. 23, 2017

(87) PCT Pub. No.: WO2016/103245
PCT Pub. Date: Jun. 30, 2016

(65) Prior Publication Data
US 2017/0209695 A1 Jul. 27, 2017

Related U.S. Application Data

(60) Provisional application No. 62/103,676, filed on Jan. 15, 2015, provisional application No. 62/028,433, filed on Jul. 24, 2014.

(51) Int. Cl.
| | |
|---|---|
| *A61N 1/00* | (2006.01) |
| *A61N 1/36* | (2006.01) |
| *A61B 18/20* | (2006.01) |
| *A61N 1/04* | (2006.01) |
| *A61N 7/00* | (2006.01) |
| *A61B 18/08* | (2006.01) |

(Continued)

(52) U.S. Cl.
CPC ........ *A61N 1/36017* (2013.01); *A61B 18/082* (2013.01); *A61B 18/1477* (2013.01); *A61B 18/203* (2013.01); *A61N 1/0456* (2013.01); *A61N 1/36021* (2013.01); *A61N 7/00* (2013.01); *A61N 7/02* (2013.01); *A61B 2018/00452* (2013.01); *A61B 2018/00601* (2013.01); *A61B 2018/00666* (2013.01); *A61B 2018/00773* (2013.01); *A61B 2018/00875* (2013.01); *A61B 2018/143* (2013.01); *A61B 2018/1425* (2013.01); *A61N 2007/0034* (2013.01); *A61N 2007/0047* (2013.01)

(58) Field of Classification Search
CPC ............ A61N 1/36017; A61N 1/36021; A61N 1/0456; A61N 2007/0034; A61B 2018/1425; A61B 2018/143
See application file for complete search history.

(56) References Cited

U.S. PATENT DOCUMENTS 6,277,116 B1 * 8/2001 Utely ..................... A61B 18/14
606/41
6,355,054 B1 3/2002 Neuberger
(Continued)

FOREIGN PATENT DOCUMENTS

WO WO 2011/011748 1/2011

*Primary Examiner* — Mallika D Fairchild
(74) *Attorney, Agent, or Firm* — Robert G. Lev

(57) ABSTRACT

A system for delivering energy into a body tissue. A tissue puncturing device is adapted to puncture a tissue surface and generate micro-channels from the tissue surface into the body tissue. A stimulator is adapted to deliver energy to the body tissue over or adjacent to the micro-channels.

25 Claims, 9 Drawing Sheets

(51) Int. Cl.
  *A61B 18/14*   (2006.01)
  *A61N 7/02*    (2006.01)
  *A61B 18/00*   (2006.01)

(56) References Cited

U.S. PATENT DOCUMENTS

| | | | |
|---|---|---|---|
| 2007/0276318 A1 | 11/2007 | Henley | |
| 2008/0045879 A1* | 2/2008 | Prausnitz | A61B 5/14514 604/20 |
| 2008/0154178 A1* | 6/2008 | Carter | A61N 1/044 604/20 |
| 2009/0222053 A1* | 9/2009 | Gaunt | A61B 5/0028 607/3 |
| 2010/0274327 A1* | 10/2010 | Carroll | A61N 1/0456 607/72 |
| 2011/0046615 A1* | 2/2011 | Manstein | A61B 18/1477 606/9 |
| 2012/0310315 A1* | 12/2012 | Savage | A61N 1/39 607/116 |
| 2014/0236258 A1* | 8/2014 | Carroll | A61N 1/36021 607/46 |
| 2014/0324113 A1 | 10/2014 | Savage et al. | |

* cited by examiner

DEVICE AND METHODS FOR DELIVERY OF STIMULATION TO A BODY TISSUE

PRIORITY INFORMATION

The present application claims priority as a national stage entry of International Application No: PCT/IL2015/050763, filed on Jul. 23, 2015, which claims priority from U.S. Provisional App. No. 62/103,676, filed on Jan. 15, 2015; and, U.S. Provisional App. No. 62/028,433, filed on Jul. 24, 2014.

FIELD OF INVENTION

This invention relates to devices for delivery of stimulation through a tissue barrier such as the skin.

BACKGROUND

The following prior art publications are considered to be relevant for an understanding of the prior art:
  U.S. Pat. No. 7,524,317 to Gruzdev et al.
  U.S. Pat. No. 8,788,045B2 to Gross
  U.S. Pat. No. 6,735,474 to Loeb
  U.S. Pat. No. 8,406,886 to Gaunt et al.
  U.S. Pat. No. 8,577,458 to Libbus et al.
  U.S. Pat. No. 6,148,232 to Avrahami Transcutaneous electrical nerve stimulation (TENS) is a non-invasive treatment which involves the placement of surface electrodes on the surface of the skin, and the use of an electric current to stimulate nerves for therapeutic purposes. Various medical devices are known that provide transcutaneous electrical stimulation using surface electrodes, for use in many kinds of treatments, such us pain relief, pain treatment, disease treatment, chronic disease treatment and rehabilitation. Penetration of an electric current through a tissue barrier, such as the skin, is limited by the resistance or impedance of the tissue, so that a tolerable electric current will typically only reach superficial nerves. Increasing the current in order to stimulate deeper nerves can result in pain, burning and irritation.

Medical devices are also known that perform percutaneous electrical nerve stimulation (PENS), which is a minimal invasive treatment, in which an ultra-fine acupuncture needle is introduced into a tissue and which penetrates into soft tissues or muscles to electrically stimulate nerve fibers. The acupuncture needle has to be inserted at the precise treatment location and sometimes causes pain and bleeding.

Other medical devices are known that puncture the stratum corneum layer of the skin in order to increase the permeability of the skin to therapeutic compounds. These devices utilize such energy sources as RF currents, ultrasonic waves, laser beams and resistive heating energy technology. These are mainly used for esthetic treatments and also as first stage for allowing transdermal delivery of large molecules such as pharmaceuticals. Such a device is disclosed, for example, in U.S. Pat. No. 7,524,317 to Gruzdev et al.

U.S. Pat. No. 8,788,045B2 to Gross describes a device which includes electrodes that are placed within 1 mm of the tibial nerve of a subject and are driven to treat polyneuropathy by driving a current into the tibial nerve. Polyneuropathy is damage or disease affecting peripheral nerves (peripheral neuropathy) in roughly the same areas on both sides of the body, featuring weakness, numbness, pins-and-needles, and burning pain.

U.S. Pat. No. 6,735,474 to Loeb describes a system for treatment of incontinence and/or pelvic pain that includes injection or laparoscopic implantation of one or more battery or radio frequency-powered micro-stimulators beneath the skin of the perineum and/or adjacent the tibial nerve. The system and method tends to reduce the incidence of unintentional episodes of bladder emptying by stimulating nerve pathways that diminish involuntary bladder contractions. The incidence of fecal incontinence is similarly reduced or eliminated.

Also known is a system for treatment of chronic pain by delivering high-frequency stimulation to sensory nerves in the peripheral nervous system to block chronic pain. An electrode is placed around a peripheral nerve and powered by a pacemaker-size generator.

A minimally-invasive system is also known that delivers percutaneous tibial nerve stimulation for treatment of overactive bladder (OAB) and the associated symptoms of urinary urgency, urinary frequency, and urge incontinence. The system is used in percutaneous stimulation to deliver to the tibial nerve electrical pulses that travel to the sacral nerve plexus, a control center for bladder function.

A system for the treatment of chronic pain of peripheral nerve origin has been disclosed in which electrical signals are transmitted transdermally through an electrode, down a lead to a target nerve. While this device might target electrical stimulation to the targeted nerve, the passage of the stimulation energy is reduced dramatically by the stratum-corneum.

U.S. Pat. No. 8,406,886 describes an implant, system and method for treating a disorder of the nervous system in a subject. The method involves using passive electrical conductors which route electrical current to electrically stimulate a target body tissue to either activate or block neural impulses depending upon the frequency and the disorder to be treated. Electrically-excitable bodily tissues such as nerves and muscles may be activated by an electrical energy applied between electrodes applied externally to the skin. Electrical energy, e.g. current, flows through the skin between a cathode electrode and an anode electrode, eliciting action potentials in the nerves and muscles underlying the electrodes. This method has been used for many years in different types of stimulators, including transcutaneous electrical nerve stimulators (TENS) which relieve pain, therapeutic electrical stimulators which activate muscles for exercise purposes, functional electrical stimulators which activate muscles for tasks of daily life and stimulators that promote regeneration of damaged bones.

U.S. Pat. No. 8,577,458 describes an implantable device for providing electrical stimulation of cervical vagus nerves for treatment of chronic cardiac dysfunction with leadless heart rate monitoring. A stimulation therapy lead includes helical electrodes configured to conform to an outer diameter of a cervical vagus nerve sheath, and a set of connector pins electrically connected to the helical electrodes. A neurostimulator includes an electrical receptacle into which the connector pins are securely and electrically coupled. The neuro-stimulator also includes a pulse generator configured to therapeutically stimulate the vagus nerve through the helical electrodes in alternating cycles of stimuli application and stimuli inhibition that are tuned to both efferently activate the heart's intrinsic nervous system and afferently activate the patient's central reflexes by triggering bi-directional action potentials.

U.S. Pat. No. 6,148,232 to Avrahami describes a device for ablating the stratum corneum epidermidis.

SUMMARY OF THE INVENTION

The present invention provides a system and method for delivering energy into a body tissue. The system of the invention comprises a tissue puncturing device that punctures the tissue surface to be treated and generates micro-channels extending from the tissue surface into the tissue below the tissue surface. The system also comprises a stimulator that delivers energy to a body tissue. The puncturing device may generate micro-channels in the tissue by any method known to puncture a tissue surface, and may involve, for example, any one or more of ultrasonic energy, laser light energy, heat energy and electrical energy. Any type of stimulation energy may be delivered by the stimulator, such as electrical stimulation, electrical nerve stimulation, and electromagnetic radiation.

As used herein, the term micro-channel refers to channels formed in a body tissue to enhance penetration of stimulation, such as electrical stimulation into the body tissue. The superficial layer of the skin, the stratum corneum, for example, is characterized by relatively high resistance and capacitance in comparison to the inner skin layers. The characteristics of resistance and capacitance are modified and/or reduced after formation of micro-channels in the stratum corneum.

The tissue puncturing device and the stimulator are under the control of a controller that includes electrical circuitry for delivery of electrical energy to the puncturing device and the stimulator.

The system of the invention also includes a processor that monitors one or more electrical or optical parameters of the tissue, such as the tissue resistance, impedance, capacitance, or optical density. When the tissue puncturing device is applied to the surface of a body tissue to be treated and is activated micro-channels are generated in a volume of the body tissue below the surface. When at least one of the optical or electrical parameters of the tissue is in a predetermined range, for example, when at least one of the optical or electrical parameters of the tissue has been reduced by at least a predetermined percentage and/or adaptive percentage of an initial value, the stimulation may be applied to the tissue. The inventor has found that puncturing of the tissue tends to modify the electrical or optical parameters of the tissue, such as resistance and capacitance, so as to reduce the current and/or the voltage or light intensity required to achieve a desired effect by the stimulator. This may also reduce the pain during stimulation and promote the penetration of the stimulation to deeper layers of the tissue.

Electrical parameters of the tissue may be measured, for example, by surface electrodes in the stimulator or by micro-needles in the puncturing device.

The tissue puncturing device may comprise one or micro-needles that are pressed into a tissue surface to be treated. In one embodiment, an electrical current is applied between two or more micro-needles for a sufficient amount of time so that at least one micro-channel is formed around a micro-needle in the tissue due to local power dissipation. This leads to ablation of tissue around the micro-needle in the outermost layers of the tissue surface, such as the stratum corneum in the case of a skin surface. In another embodiment, an ultrasound pulse waves are generated in the micro-needles to create the micro-channels. In still another embodiment, a heating module heats the micro-needles to form micro-channels in the tissue.

In another embodiment of the tissue puncturing device, electromagnetic radiation is targeted to the tissue, to generate micro-channels.

The system and method of the invention may be used in a large variety of medical and esthetic treatment, such as any of the following:

Esthetic treatment. This might be for example a facial esthetic treatment. The micro-channels and stimulation may be provided on the facial skin.

Pain relief, such as, back pain and/or carpal tunnel syndrome and/or shoulder pain. For carpal tunnel syndrome the treatment may be provided on the back side of the wrist. For back pain, the treatment may be provided on the top of the pain location area.

Delivering peripheral nerve stimulation for different treatments in the body.

Movement of the muscle or improving muscle tone. Muscle treatment may be provided in the area and on the top of the muscles.

Urinary incontinence: The treatment may be performed by stimulating the tibial nerve, more specifically the posterior tibial nerve; or the vagina.

Fecal incontinence: The treatment may be performed by stimulation of the tibial nerve.

Stimulation to activate muscles after a stroke.

Rehabilitation: Limb muscles such as the thigh or arm muscles may be stimulated. The stimulation for rehabilitation therapy may be used to buildup muscle mass in specific muscles after bone or ligament injuries. It may also be used for restoration of movements in subjects who suffer from paralysis due to spinal cord injuries and/or brain lesions, such as stroke. The functional improvement may restore, for example, grasping for supporting tasks of daily living.

Stimulation of nerves that directly or indirectly innervate various muscles. For example, stimulation may be provided on the neck, face, chest or stomach adjacent to the vagus nerve or one of its branches for the treatment of epilepsy, depression, Alzheimer's, anxiety, obesity, bulimia, tinnitus, obsessive compulsive disorder, or heart failure.

Stimulation of the vagus nerve may also be used in any of the following indications: addictions, anxiety disorders, autism, bipolar disorders, cerebral palsy, chronic headaches, cognitive impairment associated with Alzheimer's disease, coma, depression, eating disorders (e.g., anorexia and bulimia), essential tremor, fibromyalgia, heart failure, hemicrania continua, juvenile myoclonic epilepsy, migraine headaches, mood disorders, narcolepsy, obesity, obsessive-compulsive disorder, sleep disorder, tinnitus and Tourette's syndrome, hypomanic personality disorder or any other organic hypersomnia, tension type headache, alcohol-induced sleep disorders, drug-induced sleep disorders, episodic mood disorders, autistic disorder, obsessive-compulsive disorders, dysthymic disorder, alcohol dependence syndrome, drug dependence, nondependent abuse of drugs, anorexia nervosa, specific disorders of sleep of nonorganic origin, unspecified disorders of eating, tension headache, circadian rhythm sleep disorder, organic parasomnia, organic sleep disorders, essential and other specified forms of tremor, hemicrania continua, infantile cerebral palsy, migraine, cataplexy and narcolepsy, rheumatic heart failure, myalgia and myositis, sleep disturbances, polyphagia, mood, Parkinson's disease and headache. The stimulation may be performed through other nerves as well or directly to a specific location and/or organ and/or nerve in the body. The stimulation of the vagus nerve may help reset chemical imbalances in the mood centers of the brain.

Treatment of cancer, such as prostate cancer.

Control of the immune system through stimulation of the nerves.

Reduction of systemic inflammation by stimulating the vagus nerve. Vagus nerve stimulation may activate the body's natural inflammatory reflex to dampen inflammation and improve clinical signs and symptoms. The inflammatory reflex is a neurophysiological mechanism that regulates the body's immune system. It senses infection, tissue injury and inflammation and relays this information to the central nervous system, which then reflexively increases neural signaling peripherally through the vagus nerve and splenic nerve that extensively innervate the spleen and other visceral organs. The signal is transmitted to T cells in the spleen, which in turn direct effector cells including monocytes and macrophages to reduce their production of the mediators that initiate and perpetuate inflammation. Inflammation plays a significant role in acute and chronic diseases including rheumatoid arthritis, inflammatory bowel disease, psoriasis, diabetes, heart disease and multiple sclerosis.

Delivering stimulation for pain relief, effective therapy for the treatment of chronic and intractable pain including diabetic neuropathy, failed back surgery syndrome, complex regional pain syndrome, phantom limb pain, ischemic limb pain, refractory unilateral limb pain syndrome, post-herpetic neuralgia and acute herpes zoster pain, Charcot-Marie-Tooth (CMT) disease, cardiac failures/myocardial infarction, Alzheimer's, Stroke, Parkinson's disease and migraine.

Treatment of diabetic neuropathy or neuropathic pain, depression, diabetic peripheral neuropathy, accelerate healing, reduce edema, reduce pain from causes other than chronic diabetic peripheral neuropathy, treat chronic pain due to ischemia.

Treatment of soft-tissue or neuropathic pain such as, back pain, diabetic pain, joint pain, fibromyalgia, headache, reflex sympathetic dystrophy, tissue damage, sacral nerve roots or lumbosacral plexus, angina and notalgia paraesthetica.

Treatment of cervicalgia, cervical radiculopathy, cervical spasm, chronic neck pain, failed back syndrome, lumbago, lumbar muscle spasm, lumbosacral myofasciitis, lumbosacral radiculopathy, osteoarthritis of the knee, post-herpetic neuralgia, arthritis, cancer pain, cervical pain, fibromyalgia, joint pain, low back pain, migraines, post-operative pain, and sciatica.

Treatment of acute pain, post-operative pain, acute and chronic headaches, chronic low back pain, deep abdominal pain, hip fracture pain, neuropathic pain, pelvic pain, temporomandibular joint (TMJ) pain; chronic intractable pain, strength of the muscles through nerve stimulation (incontinence).

Stimulation for wound healing. Stimulation for sports to train specific muscle groups in order to train stamina and strength or to relax the muscles after an exercise session, exercise, fitness, and restoration of lost motor functions, e.g. in subjects with brain or spinal cord lesions.

Chronic pain relief or treatment, such as dorsal common most commonly used for the management of failed back surgery syndrome, angina pectoris.

Stimulation of hair growth. The micro-channels and stimulation may be provided on the scalp.

Thus in one of its aspects, the present invention provides a system for delivering energy into a body tissue, comprising:
  (a) a tissue puncturing device adapted to puncture a tissue surface and generate micro-channels from the tissue surface into the body tissue; and
  (b) a stimulator adapted to deliver energy to the body tissue.

The system of the invention may further comprise a processor configured to monitor one or more electrical or optical properties of the body tissue.

In the system of the invention, the tissue puncturing device may comprise at least one micro-needle. The puncturing device may comprise one or more matrices of one or more micro-needles. The s micro-needles may be composed of a conductive material, a semi-conductive material or an ultrasonic conductive material. One or more of the micro-needles may have a shaft that is electrically isolated to allow electrical current to only from tips of the micro-needles.

The tissue puncturing device may generate micro-channels in the tissue by utilizing any one or more of ultrasonic energy, laser light energy, heat energy and electrical energy.

The stimulator may be adapted to deliver to the body tissue any one or more of electrical stimulation, electrical current, electrical nerve stimulation, and electromagnetic radiation.

The processor may be configured to monitor one or more electrical properties of the body tissue by surface electrodes or by micro-needles in the puncturing device.

The processor may monitor one or more electrical parameters of the tissue selected from a tissue impedance, a tissue resistance, and a tissue capacitance.

The stimulator may comprise two or more electrodes in which case, the electrodes may be any one or more of a wet surface electrode a glue based surface electrode, a hydrogel surface electrode, a cotton surface electrode, or a minimal invasive electrode. At least one electrode may be incorporated into a patch having an aperture with a cover or flap, the cover or flap being configured to be raised or removed to expose a region of the tissue surface when the patch is applied to the tissue surface.

If the tissue puncturing device comprises one or more micro-needles, and the stimulator comprises two or more electrodes, the micro-needles and the electrodes may be contained in a single applicator in this case, least one of the micro-needles and at least one of the electrodes may be positioned in the applicator to allow the electrodes to contact the body surface over at least one micro-channel formed by the at least one micro-needle.

The stimulator may comprise three or more electrodes and the processor may be further configured to energize different pairs of electrodes during stimulation.

The stimulator may comprise two or more electrodes contained in a patch adapted to adhere to a body surface.

The system may further comprise a passive or active implantable conductive element.

The processor may be further configured to activate the stimulator when one or more of the monitored parameters is in a predetermined, adaptive or dynamic range.

The system may further comprise a remote control for controlling one or more of the tissue puncturing device and the stimulator.

The tissue puncturing device may be configured to ablate tissue in the micro-channels.

The wherein the stimulator may be configured to apply an electrical current to the tissue to maintain the micro-channels open. The stimulator may be adapted to stimulate two or more tissue areas simultaneously or sequentially.

In another of its aspects, the invention provides a method for delivering stimulation to a body tissue; comprising:
  (a) applying a tissue puncturing device to a body tissue surface;
  (b) activating the tissue puncturing device to puncture the tissue surface and generate micro-channels in a volume of the body tissue below the surface; and (c) delivering energy to the body tissue.

In the method of the invention, the generated micro-channels may enhance energy penetration into the body tissue and change electrical or optical parameters of the tissue.

BRIEF DESCRIPTION OF THE DRAWINGS

In order to understand the invention and to see how it may be carried out in practice, a preferred embodiment will now be described, by way of non-limiting example only, with reference to the accompanying drawings, in which.

DETAILED DESCRIPTION OF THE INVENTION

Figure 1:
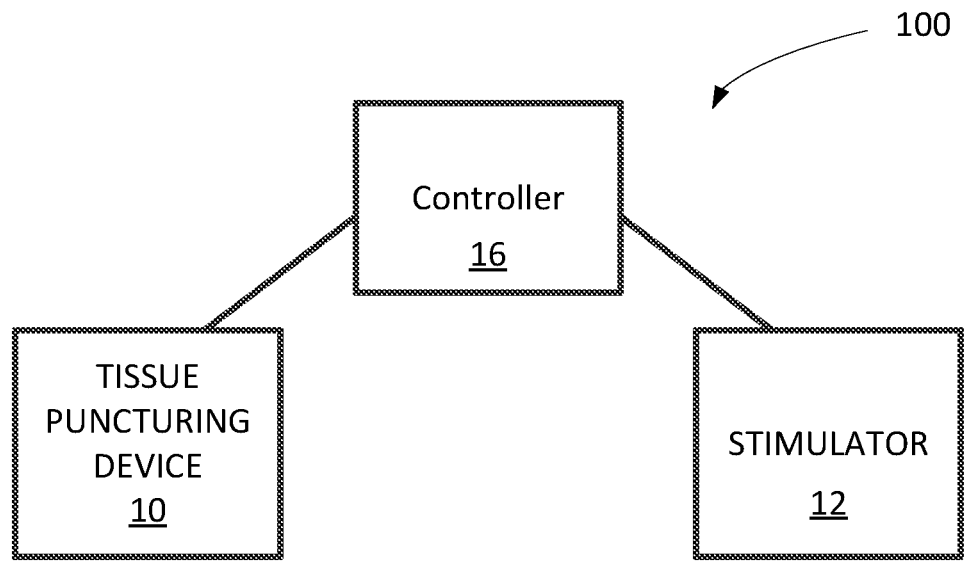
FIG. 1 shows schematically a system for delivering energy into a body tissue in accordance with one embodiment of the invention.

FIG. 1 shows schematically a system 100 for delivering energy into a body tissue, in accordance with one embodiment of the invention. The system 100 comprises a tissue puncturing device 10 and a stimulator 12. The tissue puncturing device 10 punctures the tissue surface to be treated and generates micro-channels from the tissue surface into the tissue below the tissue surface. The stimulator 12 delivers energy to a body tissue. The tissue puncturing device 10 and the stimulator 12 are under the control of a controller 16. The tissue puncturing device 10 and the stimulator 12 may be contained in separate housings, or may be contained in a single common housing.

The puncturing device 10 may generate micro-channels in the tissue by any method known to puncture a tissue surface, and may involve, for example, any one or more of ultrasonic energy, laser light energy, heat energy and electrical energy. Any type of stimulation energy may be delivered by the stimulator 12, such as electrical stimulation, such as current, electrical nerve stimulation, and electromagnetic radiation.

Figure 2:
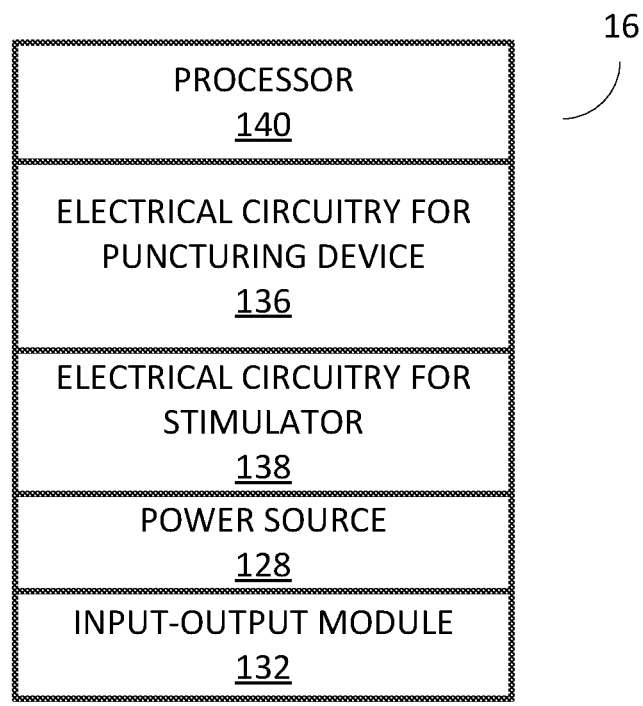
FIG. 2 shows a controller that may be used in the system of FIG. 1.

FIG. 2 shows the controller 16 in greater detail. The controller 16 includes electrical circuitry 136 for delivery of electrical energy to the puncturing device 10 and electrical circuitry 138 for delivery of electrical energy to the stimulator 12. The electrical circuitry is under the control of a processor 140 in accordance with factory set parameters or user input parameters. A power source 128 in the controller 16 energizes the processor 140 and also energizes electrical circuitry 136 and 138. A user input-output module 132, such as a keypad may be used by a user to input various parameters of the electrical energy. The input-output module 132 may include a remote control. The processor 140 also monitors some electrical or optical parameters of the tissue, such as impedance, in order to determine an extent of tissue puncturing.

Figure 3:
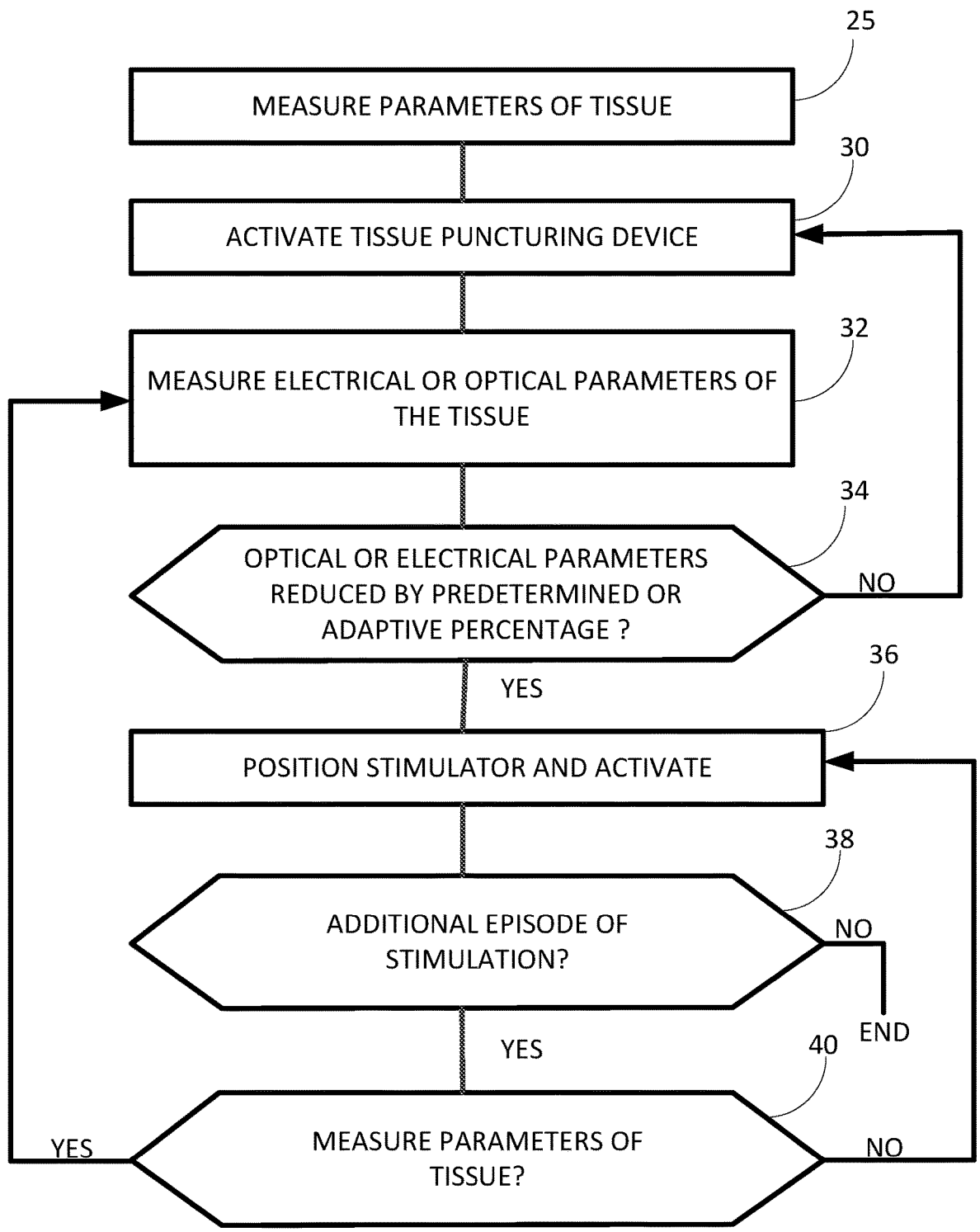
FIG. 3 shows a flow chart of a method for delivering stimulation to a body tissue in accordance with one embodiment of the invention.

FIG. 3 shows a flow chart of a method for delivering stimulation to a body tissue by the system of the invention in accordance with one embodiment of this aspect of the invention. In step 25, a preliminary determination of one or more electrical or optical parameters of the tissue is obtained, such as the tissue resistance, impedance, or capacitance. In step 30, the tissue puncturing device 10 is applied to the surface of a body tissue to be treated and is activated in order to puncture the tissue surface and generate micro-channels in a volume of the body tissue below the surface. During or following the puncturing of the body tissue, the electrical or optical parameters of the tissue are measured (step 32). In step 34, it is determined whether at least one of the optical or electrical parameters of the tissue has been reduced by at least a predetermined percentage and/or adaptive percentage of the initial values determined in step 25. Puncturing of the tissue tends to modify the electrical or optical parameters of the tissue so as to reduce the current and/or the voltage or light intensity required to achieve a desired effect in the tissue in the subsequent stimulation step. This may, also reduce the pain during electrical stimulation and promote the penetration of the stimulation to deeper layers of the tissue. If at least one of the optical or electrical parameters of the tissue has not been reduced by at least a predetermined or adaptive percentage of the initial values determined in step 25, the process returns to step 30 with reactivation of the tissue puncturing device. The tissue puncturing device may be activated in the same location or in a different location than before. If at least one of the optical or electrical parameters of the tissue has been reduced by at least a predetermined or adaptive percentage of the initial values determined in step 25, the process continues to step 36 in which the stimulator is positioned on the tissue surface over and/or partially over and/or adjacent to the punctured region of the tissue surface, and is activated. The positioning may also be, performed before or during the puncturing (step 30), and is possibly displaced or removed during the puncturing. At the end of the stimulation episode or during the stimulation episode, it is determined in step 38 whether an additional episode of stimulation is required. If yes, then in step 40, it is determined whether the electrical or optical properties of the tissue are to be measured again. Additional micro-channels may be necessary after the first episode of the stimulation, for example, when the original micro-channels have sealed or the electrical or optical parameters of the tissue are no longer reduced by the predetermined or adaptive percentage. If yes, then the process returns to step 32 with the measurement of the optical or electrical properties of the tissue. Otherwise, the process returns to step 36 with the activation of the stimulator. If at step 38 it is determined that an additional episode of stimulation is not required, then the process terminates. During the stimulation applied in step 36 the optical or electrical parameters of the tissue may be measured periodically, and if the reduced parameters returned to initial values as determined in step 25, process returns to step 32 (not shown in the figure).

Electrical parameters may be measured by surface electrodes in the stimulator or by micro-needles in the puncturing device.

In the case of electrical stimulation, a biocompatible conductive material may be applied to the tissue surface before or during the stimulation.

Figure 4:
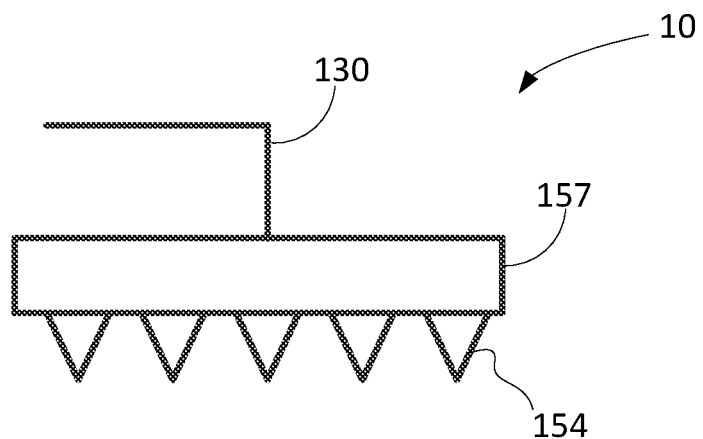
FIG. 4 shows an applicator that may be used in tissue puncturing device for use in a system for delivering energy into a body tissue in accordance with one embodiment of the invention.

The tissue puncturing device 10 may include an applicator 157 shown in FIG. 4. The applicator 157 contains one or more matrices of two or more micro-needles 154 to generate at least one micro-channel. The micro-needles 154 are connected to the electric circuitry 136 by one or more electrical connections 130. The micro-needles 154 may be composed of a conductive material or semi-conductive material. When the micro-needles are pressed into a tissue surface to be treated, and current is applied between two or more micro-needles for a sufficient amount of time, at least one micro-channel is formed around a micro-needle in the tissue due to local power dissipation. This leads to ablation of tissue around the micro-needle in the outermost layers of the tissue surface, such as the stratum corneum in the case of a skin surface.

Each micro-needle matrix can generate at least one micro-channel and/or a separate cluster of micro-channels in the tissue. Each matrix may cover an area of up to 1000 cm$^2$ of the tissue surface. One or more clusters of micro-channels may be generated simultaneously or sequentially. Two micro-needles may be located on the same matrix. All of the micro-needles may be applied to the tissue surface simultaneously, and may be electrically activated simultaneously or sequentially. Closely located micro-needles are preferentially activated simultaneously, in order to effectively generate the micro-channels. Alternatively, different combinations of the micro-needles may be applied to the tissue surface and activated simultaneously or sequentially. Puncturing the tissue surface may be performed more than one time in a single treatment session, for example, when the area to be punctured is larger than the micro-needle matrix size, or when several discrete regions on the tissue surface are to be punctured, or when some or all of the micro-channels have sealed during the treatment.

The micro-needle length may be, for example 10-400 μm and the diameter may be, for example, 10-400 μm, which tends to prevent bleeding and pain. The micro-needles may be conic or cylindrical or any other shape that allows the puncturing and/or ablation of the superficial tissue layers. When the outermost layers of the tissue barrier are extremely thick in the treatment location, as, for example, in some individuals, larger micro-needles may be used. The micro-needles may have a spacing of about 0.01-10 mm. The micro-needles may or may not be uniformly distributed in the matrix. A widely spaced distribution of the micro-needles matrix may reduce redness and swelling of the skin.

The applied current between adjacent micro-needles may be a direct current (DC) or an alternating current (AC) with a frequency, for example, of 1 kHz-100 MHz, or RF and a duration of 0.001-1,000 msec, and a pause of 0.001-1,000 msec. The shaft of the micro-needles may be electrically isolated to allow electrical current only from the tips of the micro-needles, and in order to reduce the current in superficial layers of the tissue being treated.

The processor 140 monitors the electrical parameters of the tissue, such as impedance, in order to determine an extent of puncturing of the tissue. The formation of the micro-channels may be regulated in response to parameters measured during micro-channel formation, such as the tissue impedance and/or conductivity and/or voltage and/or current. The values of these parameters may be selected based on various parameters of the subject, and may be dynamic. A conductivity threshold may be specified that; when reached, indicates that micro-channel generation is completed. The processor may adjust the current or voltage applied through at least one of the micro-needles in response to changes in electrical parameters in one of the micro-needles.

During and after the creation of the micro-channels, an extracellular fluid may be introduced into the micro-channels, which reduces the impedance along the micro-channels. This may reduce the power required for the stimulation, especially electrical stimulation, and allow deeper penetration of the stimulation energy.

Figure 5:
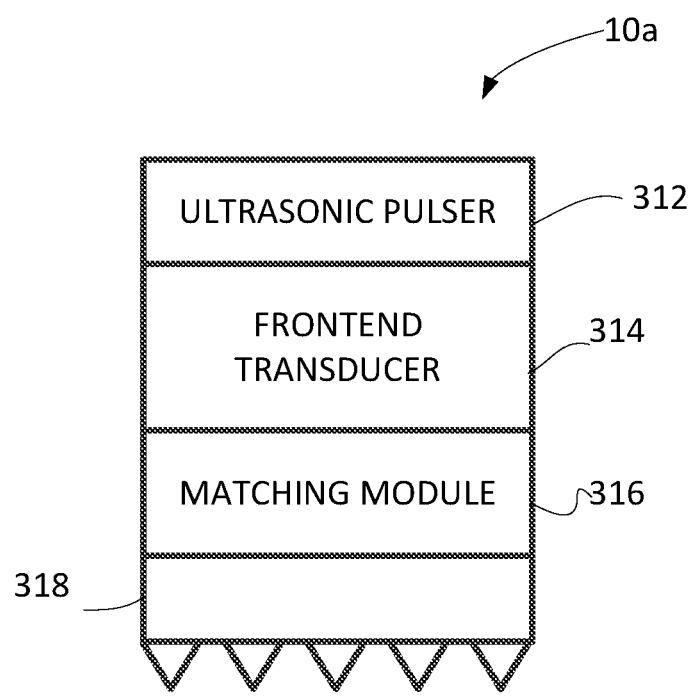
FIG. 5 shows a tissue puncturing device that may be used in a system for delivering energy into a body tissue in accordance with one embodiment of the invention.

FIG. 5 shows a tissue puncturing device 10a that may be used in the system 100 in accordance with another embodiment of the invention. The device 10a comprises an ultrasonic pulser 312 and includes electronics, software and a feedback mechanism that generate electrical signals that are transferred to the frontend 314. Frontend 314 includes a transducer that converts the electrical signals into ultrasound pulse waves. Matching module 316, allows a suitable physical connection between the micro-needle plate 318 and the frontend 314. Micro-needle plate 318 comprises at least one micro-needle or a matrix of micro-needles or a cluster of matrices. The micro-needle plate 318 may be removable to allow using different shapes of plates and/or when moved from one subject to another. The input-output module 132 can be used to allow a user to input selectable parameters of the puncturing, such as the timing and energy, so that minimal heating and/or pain is sensed by the subject, while micro-channels are generated.

Several modes of operation for transferring the ultrasound pulse waves to the micro-needles are available. For example, a single transducer that transmits ultrasound pulse waves to the micro-needle-plate may be used, with the ultrasound pulse waves being distributed to the micro-needles from which they precede tissue. As another example, the device 10a may include an array of ultrasound transducers configured to generate ultrasound pulse waves in various combinations of micro-needles. This allows different combinations of micro-needles to be activated at different times or with different parameters. Micro-channel generation may be performed simultaneously or sequentially by different sets of micro-needles. Electric signals can be applied through one or more of the micro-needles, and electric parameters can be measured in order to adjust the ultrasonic energy of the micro-needles.

The frequencies of the ultrasound pulse waves may be, for example, in the range of 1 kHz-50 MHz and the intensities may be in the range of 0.1-5 W/mm$^2$. The energy transmitted by each micro-needle can be between 0.01-100 Joule/channel. The frequency and intensity of the ultrasound pulse waves may be varied from one subject to another, and also in the same subject, due to anatomical and physiological differences. The interval time of the pulses may be less than one second, in order to reduce or prevent overheating of the tissue.

The micro-needle-plate and the micro-needle/s can be made, for example from titanium or aluminum, or other metal or material compatible with delivering ultrasound pulse waves. The micro-needles may also be conductive in order to deliver electric energy and/or to measure electric parameters that provide an indication regarding the extent of micro-channel generation.

Figure 6:
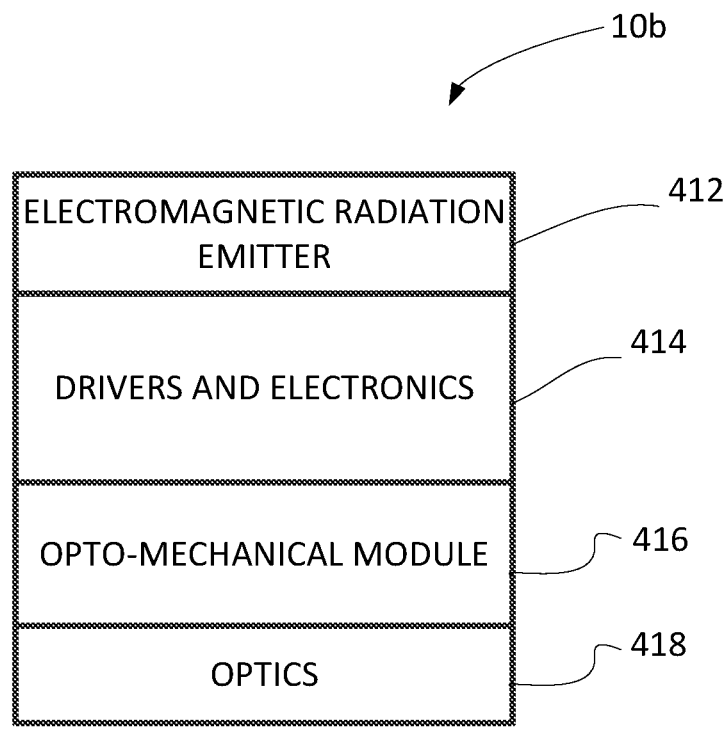
FIG. 6 shows a tissue puncturing device that may be used in a system for delivering energy into a body tissue in accordance with a second embodiment of the invention.

FIG. 6 shows an example for a tissue puncturing device 10b that may be used in the system 100 in accordance with yet another embodiment of the invention. The device 10b includes an electromagnetic radiation emitter module 412, such as a laser that generates the energy for the formation of the micro-channels. The power source 128 provides the energy for the electromagnetic radiation emitter module 412. Drivers and electronics 414 control the emitter module 412. The input output device module 132 allows selection of the electromagnetic radiation parameters, such as the duration and intensity of electromagnetic pulses.

Micro-channels may be generated by activation of an opto-mechanical lens and/or mirrors 416 and optics 418 that allow targeting the electromagnetic radiation energy to the targeted tissue, with sufficient energy to generate micro-channels and also aiming of the beam along the tissue to allow generation of a plurality of micro-channels. The micro-channels may have a diameter 1-1000 μm, and distance spacing of 5-5000 μm. Surface electrodes, not shown in FIG. 6, may also be used for measurement of electric parameters of the tissue to provide an indication of the extent of micro-channel formation.

Figure 7:
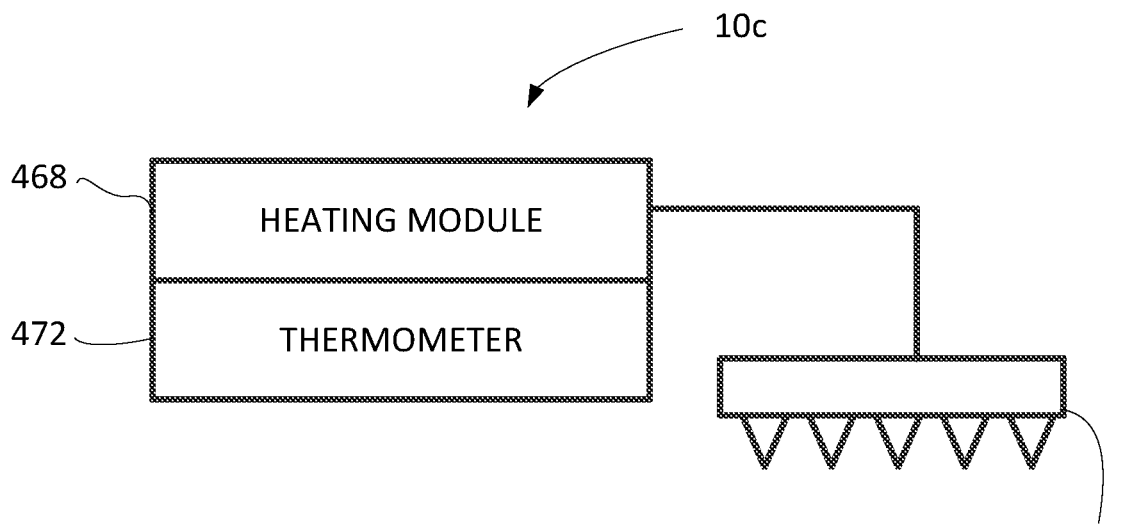
FIG. 7 shows a tissue puncturing device that may be used in a system for delivering energy into a body tissue in accordance with a third embodiment of the invention.

FIG. 7 shows a tissue puncturing device 10c that may be used in the system 100 in accordance with still another embodiment of the invention. The power source 128 provides energy to a heating module 468. The input and output module 132 allows control of the heating parameters, such as the time duration and temperature. The processor 140 controls the device, including the heating module. The device may also include a thermometer that measures the temperature in the micro-needle plate 474, which includes at least one micro-needle, in order to prevent over-heating of the tissue. The micro-needles are designed to conduct heat which may be dissipated from the tips and which may be applied for different interval times. The temperature of the applied heating may be in the range of 34-80° C.

Figure 8:
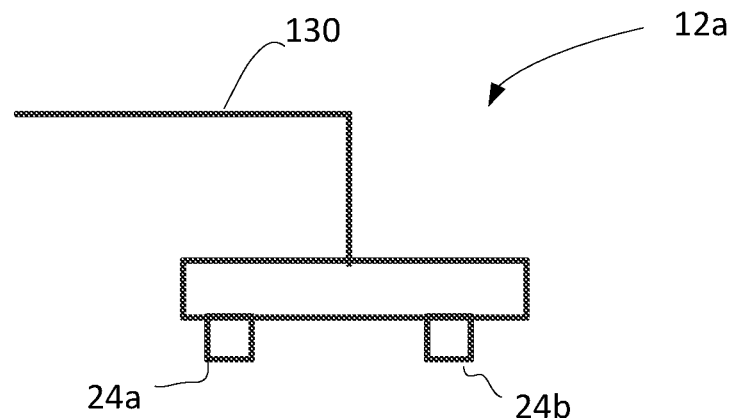
FIG. 8 shows an electrical stimulator that may be used in a system for delivering energy into a body tissue in accordance with one embodiment of the invention.

FIG. 8 shows an electrical stimulator 12a that may be used in the system 100 in accordance with one embodiment of the invention. The stimulator 12a includes two or more electrodes 24. Two electrodes 24a and 24b are shown in FIG. 8. This is by way of example only, and the device 12a may include any number of electrodes as required in any application. The electrodes 24 may be surface electrodes adapted for application onto a body surface, or minimal invasive electrodes adapted for penetration into a tissue surface. In case of minimal invasive electrodes, micro-needles in the puncturing device may be adapted to also function as minimal invasive electrodes. The electrodes may be, for example, wet (liquid/water based), glue based hydrogel electrodes or cotton electrodes. The power source 128 energizes the electrical circuit applying an alternating or direct voltage signal or an alternating or direct current signal across the electrodes 24 via electrical connections 130. The input-output module 132 may be used by a user to input various parameters of the electrical stimulation, such as the voltage across the electrodes, the current, pulse frequency, pulse duration, periodicity of electrical impulses, pulse type, and the timing of the electrical stimulation. Energization of the electrodes may be switched between different pairs of stimulation electrodes during the stimulation. The processor 140 controls the electrical circuit for energizing of the electrodes 24, in accordance with factory set parameters and user input parameters. The processor may also be used to monitor the electrical signals and parameters which are measured by the device. The electrical stimulation, when applied following the formation of micro-channels, may help to prevent sealing of the micro-channels and therefor allow a prolonged period of treatment.

Figure 9:
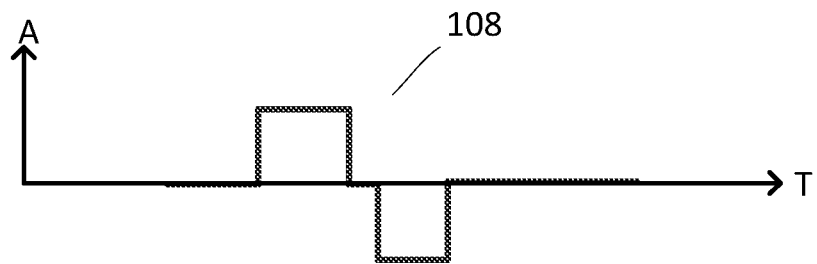
FIG. 9 shows one cycle of an exemplary electrical signal that may be used in the invention.

The electrical stimulation may be current-controlled or voltage controlled. The electrical current pulses may be symmetric or asymmetric as required in any application. The pulses may be charged balanced bi-phasic pulses. The stimulation may have a frequency of 0.01-10,000 Hz, a current amplitude of 0.001-100 mA, a pulse width of 1-2000 μsec and a voltage of up to 600 Volts. Signal 108, shown in FIG. 9, shows one cycle of an exemplary electrical signal that may be used.

The distance between the electrodes may be determined by the depth and location of the tissue to be treated. In general, the deeper the tissue to be treated beneath the body surface, the greater the required distance between the electrodes. The distance between the electrodes may be dynamic, and determined on-the-fly.

Figure 10:
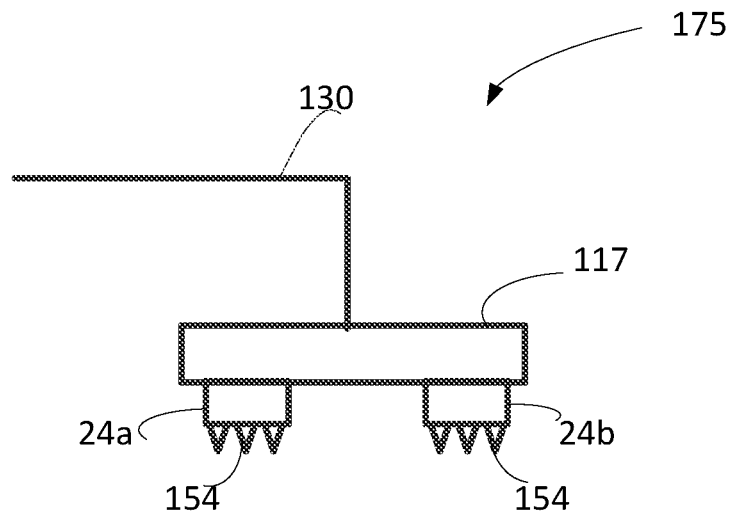
FIG. 10 shows a system for puncturing a tissue surface and applying electrical stimulation to the tissue surface in which tissue puncturing and electrical stimulation is performed using a single applicator.

FIG. 10 shows a system 175 for puncturing a tissue surface and applying electrical stimulation to the tissue surface in which tissue puncturing and electrical stimulation is performed using a single applicator 117 that may be a hand held applicator. The applicator 117 contains two or more electrodes 24 and one or more matrices of micro-needles 154. At least one electrode is placed over or partially over or near at least one generated micro-channel. Two electrodes 24a and 24b are shown in FIG. 10. This is by way of example only, and the applicator 117 may include any number of electrodes as required in any application. The electrodes 24 may be surface electrodes adapted for application onto a tissue surface, or minimal invasive electrodes, in which case, the micro-needles 154 may be adapted to also function as minimal invasive electrodes. The power source 128 energizes the electrical circuit 136 that delivers electrical energy to the micro-needles as well as the electrical circuit 138 that delivers electrical energy through the electrodes 24 via electrical connections 130 in accordance with factory set parameters or user input parameters. The input-output module 132 may be used to input various parameters of the puncturing and electrical stimulation, such as the voltage across the micro-needles and/or electrodes, the current, frequency, duration, periodicity of electrical pulses, and the timing of the electrical stimulation. The processor 140 may also monitor the tissue impedance or other electrical parameters in order to determine an extent of puncturing of the tissue. The micro-needles 154 may or may not be removed from the applicator after puncturing prior to energizing the electrodes. The micro-needles 154 may not be removed, after insertion of the micro-needles into the tissue, and participate in the electrical stimulation process together with electrodes 24 and therefore electrical stimulation may be provided through the micro-needles as well. Switching between the puncturing and stimulation configurations may be performed mechanically or electrically.

Figure 11A:
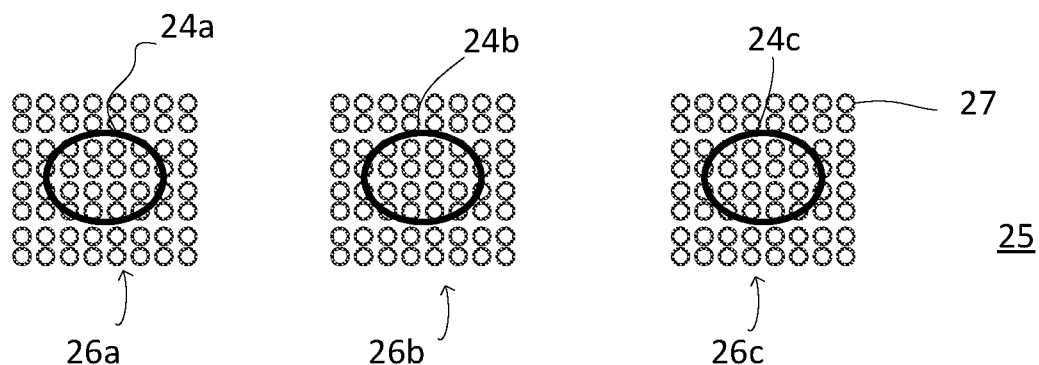
FIG. 11a shows a tissue surface in which three clusters of micro-channels and each cluster of micro-channels extends beyond the contact area of a corresponding electrode.
Figure 11B:
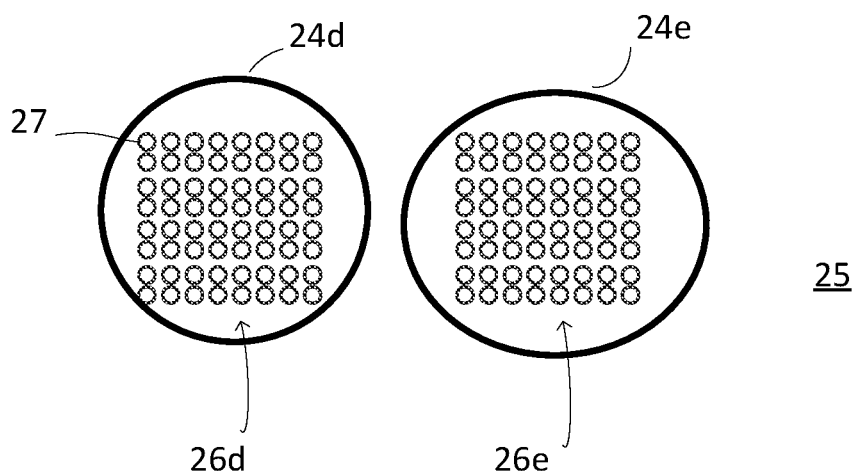
FIG. 11b shows a tissue surface in which two clusters of micro-channels were generated and the area of contact of each electrode extends beyond the corresponding cluster of micro-channels.
Figure 11C:
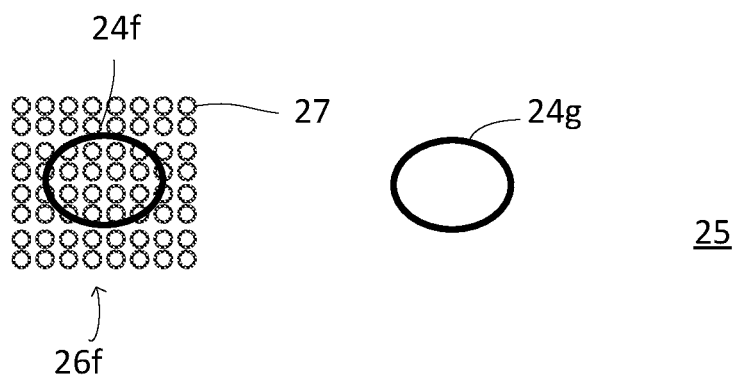
FIG. 11c shows a tissue surface in which one cluster of micro-channels was generated beneath the contact area of an electrode.

The location of the application of the stimulation relative to the location of the micro-channels may be determined as required in any application. In general, when the electrodes are placed on the tissue surface over the micro-channels, the stimulation tends to be more effective. Less energy is needed for the stimulation, and the stimulation may penetrate deeper into the tissue. This may reduce pain, increase the effectiveness of treatment, and shorten the treatment time. FIG. 11a shows, as a first example, a tissue surface 25 in which three clusters 26a, 26b, and 26c of micro-channels 27 were generated. Also shown is the boundary of the contact area 24a, 24b, and 24c of three electrodes on the tissue surface 25. In this example, each cluster of micro-channels extends beyond the contact area of the corresponding electrode. FIG. 11b shows, as a second example, the tissue surface 25 in which two clusters 26d and 26e of micro-channels 27 were generated. Also shown is the boundary of the contact area 24d, and 24e of two electrodes on the tissue surface 25. In this example, the area of contact of each electrode extends beyond the corresponding cluster of micro-channels. Since the resistance in the micro-channels is lower than the non-punctured tissue regions in contact with the stimulation electrodes 24, it is expected that most of the current will flow through the micro-channels during the stimulation. FIG. 11c shows as a third example, the tissue surface 25 in which one cluster 26f of micro-channels 27 was generated beneath the contact area 24f of an electrode. Micro-channels are not present under the contact area 24g of a second electrode. Any combination of the above examples is possible, with any number of electrical electrodes and micro-channel clusters.

Figure 12:
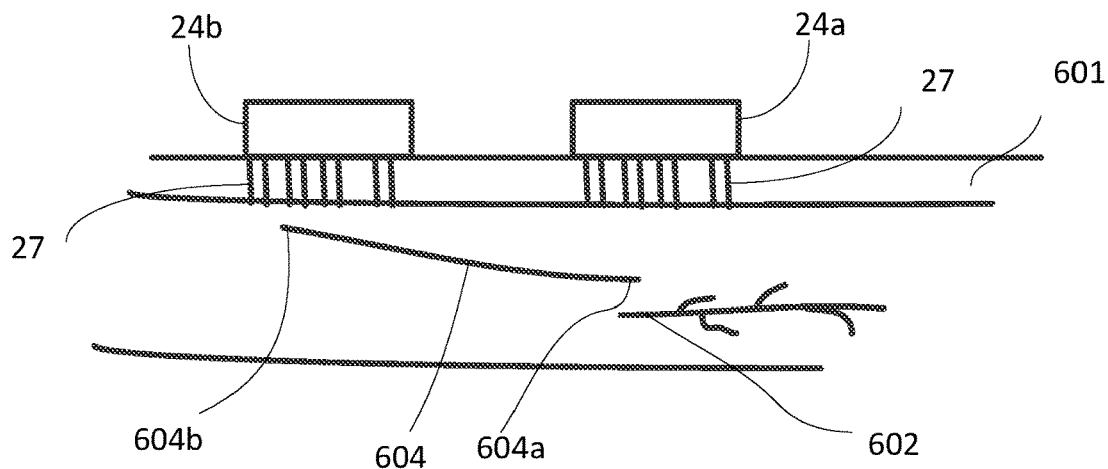
FIG. 12 shows delivering of stimulation energy to either activate block neural impulses to a targeted tissue.

FIG. 12 shows use of the system 100 for delivering stimulation energy to either activate or block neural impulses to a targeted tissue 602. An implantable conducive element 604 is implanted beneath the tissue with one side of the conductive implant located close to the tissue surface and to the electrodes 24 and the other side of the conductive implant located in proximity to the targeted tissue 602. Micro-channels 27 are generated under or adjacent to at least one of the electrodes. In this example, the micro-channels ablate the surface tissue, the stratum-corneum 601, and allow delivery of the stimulation energy, and more specifically, electrical stimulation energy, such as current, from the electrodes 24 through the conductive implant 604 to the targeted tissue, such as nerve, 602. The conductive implant may be passive or may have active element that stores stimulation energy or modifies or amplifies the intensity of the energy to be delivered to the targeted tissue. The device may be used in the treatment of a disorder of the nervous system, in which case, the targeted tissue may be a nerve, One electrode is positioned over the pick-up end 604b of the implant conductor 604 and current is conducted from the end 604b of the implant to the end 604a which provides the stimulation to the target body tissue 602. The current then flows through the target body tissue and then flows to the other surface electrode through body tissues, to stimulate the targeted body tissue 602.

The applicator of the system may be in the form of a patch configured to adhere to a body surface. A patch type applicator might be useful when prolonged stimulation is desired.

Figure 13:
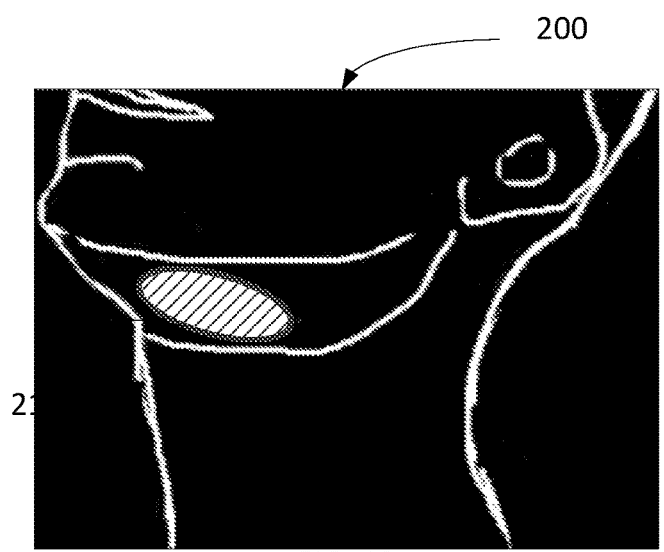
FIG. 13 shows an individual having an applicator applied to a skin surface.

FIG. 13 shows an individual 200 having an applicator 210 applied to a skin surface. As explained below, a patch applicator may be used, for example, in the treatment of sleep disorders, such as obstructive sleep apnea and snoring, as well as in male impotence, an overactive bladder, pain relief or neuropathy pain relief. The electrical stimulation may also be delivered to the target tissue via an implanted lead located between the applied stimulation and the target tissue (not shown in FIG. 13).

Figure 14:
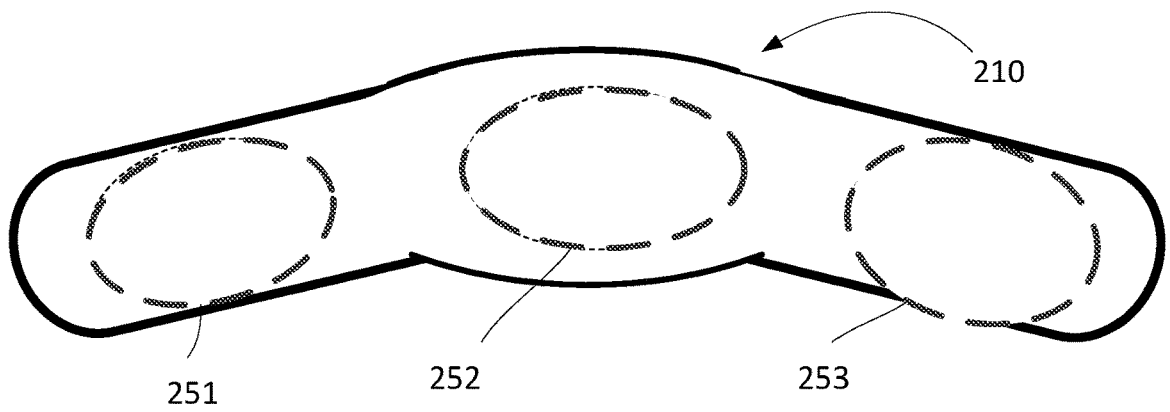
FIG. 14 shows a configuration of the patch of FIG. 13 that includes three electrodes that may be activated simultaneously or sequentially in pairs.

FIG. 14 illustrates a configuration of the patch 210. The patch 210 includes three electrodes 251, 252, and 253; that may be activated simultaneously or sequentially in pairs. The patch may include all electronics and/or part of the electronics, or could be connected by wires to external electronics. Micro-channels may be generated beneath the location of at least one of the electrodes.

For the treatment of obstructive sleep apnea or snoring, the applicator 210 in the form of a patch may be affixed, as shown in FIG. 14, on the front of the neck, underneath the chin or underneath the subject's submental triangle so that the electric current passes through the hypoglossal nerve, and adequate energy is applied to cause forward movement of the tongue. The largest of the pharyngeal muscles responsible for upper airway dilation is the genioglossus muscle. This muscle is responsible for forward tongue movement and the stiffening of the anterior pharyngeal wall. The right and left sided hypoglossal nerves innervate the right and left sided gengioglossus muscles, respectively. Electrical stimulation of only one sided hypoglossal nerves can pull the tongue forward. Contraction of the pharyngeal muscles opens the airway to restore proper breathing by pulling the tongue forward.

A pattern of stimulation in which different pairs of electrodes are activated sequentially may allow periodic relaxation of the muscles. For example, electrode 252, located in between electrodes 251 and 252, may be activated with electrode 251, which may be applied to one side of the neck, and the electrode 252 may be activated with electrode 253, which may be applied to the other side of the neck, and so on. Alternatively, the patch may include only electrodes 252 and 251, or only electrodes 252 and 253, in which case only the nerve on one side of the neck is stimulated. It may also include only electrodes 251 and 253. The patch 210 may be used in a system of the invention that includes a sensor which detects an indication of a sleep disorder such as snoring or apneas. The system may also include a sensor which detects any indication of a sleep disorder and/or rhythm of breathing to allow non-continuous activation of the stimulation.

Figure 15:
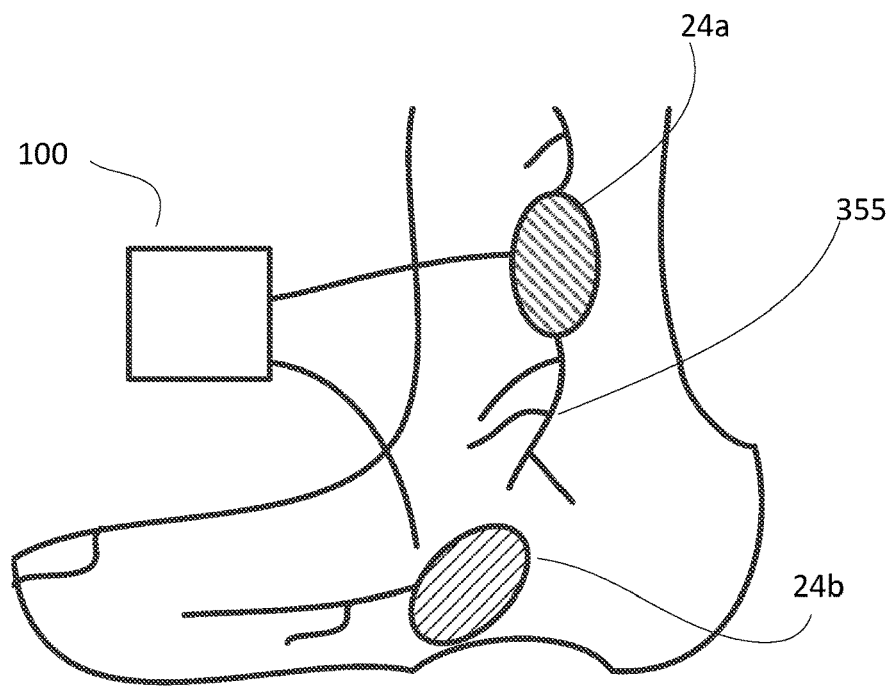
FIG. 15 shows use of the invention in the treatment of neuropathic pain or overactive bladder.

FIG. 15 shows use of the system of the invention in the treatment of chronic pain such as peripheral neuropathy pain or polyneuropathy, or polyneuropathy pelvic pain or overactive bladder (OAB) and the associated symptoms of urinary urgency, urinary frequency, and urge incontinence. The system is used to stimulate the tibial nerve. The tibial nerve 355, is a branch of the sciatic nerve; and terminates in the foot. Micro-channels are generated in the skin in the area where at least one of the electrodes 24a and 24b is to be affixed; and electrodes 24a and/or 24b are placed over the tibial nerve in a way that maximum stimulation energy, such as electrical energy, is driven to the tibial nerve. The micro-channels ablate the stratum-corneum and allow maximal penetration of the electrical energy into the tibial nerve. Electrodes 24a and 24b may be affixed, as shown in FIG. 15, in proximity to the ankle, such that the energy, such as electric current, passes through the tibial nerve, and adequate energy, such as current, is applied to tibial nerve 355. The electrodes may be positioned in proximity to the ankle where the tibial nerve is relatively close to the skin surface. The electrodes may be replaced from one treatment episode to the other. For some applications, a subject may be treated using the device, either at home or in the clinic, for 30 min, once or twice a week, and for a period of about twelve weeks. For some applications, treatment is administrated to the subject one or more times a day, for a period of up to a few months. For some applications treatment is administrated to the subject continuously. The location of the posterior tibial nerve, may be determined by techniques that are known in the art; such as by observing a movement of the toe. The electrical stimulation may be delivered to the target tissue via an implanted lead located between the applied stimulation and the target tissue.

Figure 16:
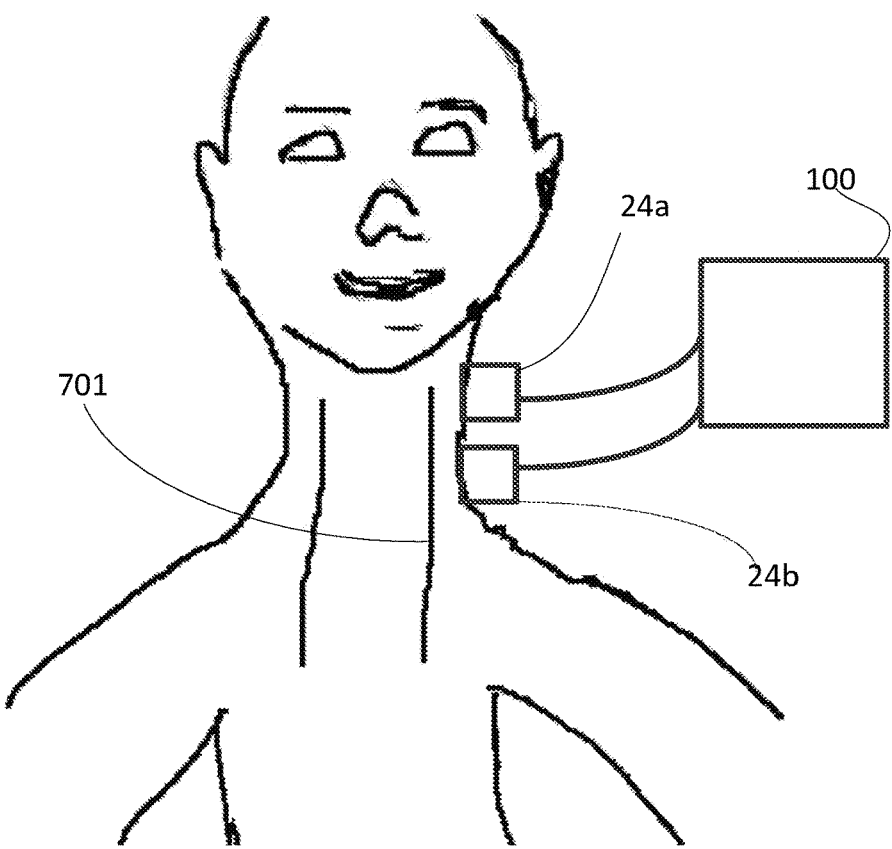
FIG. 16 use of the invention in the treatment of disorders such as epilepsy, high blood pressure.

As shown in FIG. 16, for the treatment of disorders such as epilepsy or high blood pressure, micro-channels can be generated in the skin over the vagus nerve 701 and electrodes 24 placed on the skin over the vagus nerve to allow the treatment.

Figure 17:
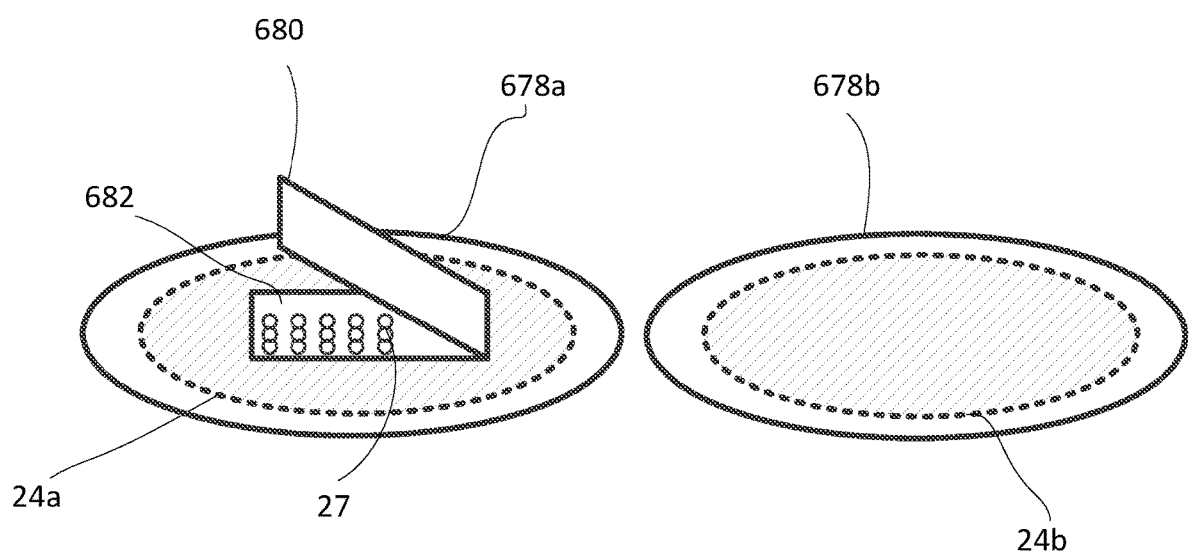
FIG. 17 shows a patch that may be used in the invention having a flap that can be raised to expose a region of the underlying tissue surface when the patch is applied to the tissue surface.

FIG. 17 shows a patch 678a that may be used in the system 100. The patch 678a is adapted to be placed on a tissue surface. The patch includes a flap 680 that can be raised to expose a region 682 of the underlying tissue surface when the patch is applied to the tissue surface. One or more electrodes 24a (indicated by phantom lines in FIG. 17) are affixed to the underside of the patch 678a. A second electrode 24b, may be affixed on the underside of the patch 678a, or, as shown in FIG. 17, the underside of a separate patch 678b. After application of the patch 678a to the tissue surface, the flap 680 may be opened to expose the region 682 of the tissue surface, and the tissue puncturing device may be applied to the exposed region 682 of the tissue surface, and micro-channels 27 formed in the region 682. The tissue puncturing device can then be removed and the flap 682 closed. In this way, the electrode 24a is positioned over the punctured region 682 of the tissue surface, and stimulation energy can be delivered directly to the punctured tissue.

For the treatment of male impotence, the applicator in the form of a patch may be placed on the skin over nerves that innervate the male genitalia and control erection such as the cavernous nerves and the dorsal nerve. The treatment may also enhance blood flow to the penis.

For enhancing blood flow, the applicator may be placed on a tissue surface, in an area of reduced blood flow, or over an area that affects blood flow in another location in the body.

For wound treatment, such as chronic wounds the applicator may be placed on or near a wound. The treatment may involve applying different types of electrical stimulation. The electrical stimulation may involve high voltage pulsed current (HVPC).

Treatment of a neurological disorder in the face such as Bell's Palsy may be carried out using the invention through stimulation of facial nerves.

Esthetic treatment, such as cellulite reduction may be performed by stimulating the skin over the cellulite to be reduced. This treatment may also reduce signs of aging by maintaining or increasing muscle tone stimulating collagen, elastin, and adenosine triphosphate (ATP) production and enhancing facial muscle tone may increase skin elasticity and smooth lines, wrinkles and texture irregularities. It may also provide muscle tissue with the nutrients to maintain muscle tone by increasing blood flow to the tissue.

The invention claimed is:

1. A system for delivering penetrating electrical energy into selected body tissue, comprising:
   (a) a tissue puncturing device adapted to puncture a tissue surface at a selected site and generate open micro-channels from the tissue surface into the selected body tissue; and
   (b) a stimulator, operating separately from said tissue puncturing device, and comprising one or more surface electrodes as a sole source of penetrating electrical energy for said selected body tissue, wherein at least one surface electrode is positionable in contact with the tissue surface over at least one of the open micro-channels at said selected site to deliver penetrating electrical energy through said at least one open micro-channel when said puncturing device is not puncturing the selected body tissue.

2. The system according to claim 1 further comprising a processor operatively connected to said stimulator, and configured to monitor one or more electrical or optical properties of the body tissue during the delivery of the electrical energy through the microchannels by the stimulator.

3. The system according to claim 2 wherein the tissue puncturing device comprises at least one micro-needle.

4. The system according to claim 3 wherein the tissue puncturing device comprises one or more matrices of one or more micro-needles.

5. The system according to claim 4 wherein the micro-needles are composed of a conductive material, a semi-conductive material or an ultrasonic conductive material.

6. The system according to claim 5 wherein one or more of the micro-needles has a shaft that is electrically isolated to allow electrical current only from tips of the micro-needles.

7. The system according to claim 4 wherein the tissue puncturing device comprises one or more micro-needles, and the micro-needles and the electrodes are contained in a single applicator.

8. The system according to claim 7 wherein at least one of the micro-needles and at least one of the electrodes are positioned in the applicator to allow the electrodes to contact the body surface over at least one micro-channel formed by the at least one micro-needle.

9. The system according to claim 3 wherein the tissue puncturing device generates micro-channels in the tissue by utilizing any one or more of ultrasonic energy, laser light energy, heat energy and electrical energy.

10. The system according to claim 2 wherein the processor is configured to monitor one or more electrical properties of the body tissue by surface electrodes or by micro-needles in the puncturing device.

11. The system according to claim 10 wherein the surface electrodes are any one or more of a wet surface electrode, a glue based surface electrode, a hydrogel surface electrode, a cotton surface electrode, or a minimal invasive electrode.

12. The system according to claim 11 wherein at least one electrode is incorporated into a patch having an aperture with a cover or flap, the cover or flap being configured to be raised or removed to expose a region of the tissue surface when the patch is applied to the tissue surface.

13. The system according to claim 2 wherein the processor monitors one or more electrical parameters of the tissue selected from a tissue impedance, a tissue resistance, and a tissue capacitance.

14. The system according to claim 2 further comprising a conductive element configured to be implanted in the body.

15. The system according to claim 2 wherein the processor is further configured to activate the stimulator when one or more of the monitored parameters is in a predetermined adaptive or dynamic range.

16. The system according to claim 2 further comprising a remote control for controlling one or more of the tissue puncturing device and the stimulator.

17. The system according to claim 2 wherein the tissue puncturing device is configured to ablate tissue in at least one of the micro-channels.

18. The system according to claim 17 wherein the stimulator is configured to apply an electrical current to the tissue to maintain the micro-channels open.

19. The system according to claim 18 wherein the stimulator is adapted to stimulate two or more tissue areas simultaneously or sequentially.

20. The system according to claim 19 wherein the puncturing device and the stimulator are contained in a single common housing.

21. The system according to claim 1 wherein the stimulator is adapted to deliver to the body tissue any one or more of electrical stimulation, electrical current and electrical nerve stimulation.

22. The system according to claim 21 wherein the stimulator comprises three or more electrodes and the processor is further configured to energize different pairs of electrodes during stimulation.

23. The system according to claim 21 wherein the stimulator comprises two or more electrodes contained in a patch adapted to adhere to a body surface.

24. A method for delivering penetrating electrical energy into a selected body tissue; said method comprising:
   (a) applying a tissue puncturing device to a surface of said selected body tissue at a selected site and forming open micro-channels in the tissue;
   (b) removing said tissue puncturing device from said selected site and leaving open said micro-channels in said body tissue below the surface at said selected site; and
   (c) placing at least one surface electrode on at least one said micro-channel, and delivering penetrating electrical energy exclusively from said at least one surface electrode via said at least one open micro-channels to said selected body tissue at said selected site.

25. The method according to claim 24 wherein the generated micro-channels enhance energy penetration into the body tissue and change electrical or optical parameters of the tissue.

\* \* \* \* \*